United States Patent
Golub et al.

(10) Patent No.: US 10,441,739 B1
(45) Date of Patent: Oct. 15, 2019

(54) MULTI-FUNCTIONAL DEVICE HAVING AN INTERCHANGEABLE OPTION FOR A SPRING-LOADED VALVE FOR DELIVERING INHALING MEDICAL GAS AND/OR NEBULIZED MEDICINE TO A SPONTANEOUSLY BREATHING PATIENT

(71) Applicants: Michael Golub, Boca Raton, FL (US); Svetlana Golub, Boca Raton, FL (US)

(72) Inventors: Michael Golub, Boca Raton, FL (US); Svetlana Golub, Boca Raton, FL (US)

(*) Notice: Subject to any disclaimer, the term of this patent is extended or adjusted under 35 U.S.C. 154(b) by 764 days.

(21) Appl. No.: 14/659,813

(22) Filed: Mar. 17, 2015

(51) Int. Cl.
*A61M 16/08* (2006.01)
*A61M 16/14* (2006.01)
*A61M 16/12* (2006.01)
*A61M 16/20* (2006.01)

(52) U.S. Cl.
CPC ........ *A61M 16/0833* (2014.02); *A61M 16/12* (2013.01); *A61M 16/14* (2013.01); *A61M 16/20* (2013.01)

(58) Field of Classification Search
CPC .......... A61M 16/0816; A61M 16/0833; A61M 16/12; A61M 16/208; A61M 2039/0027; A61M 2039/1016; A61M 2039/1094; A61M 2039/242; A61M 39/00; A61M 39/10; A61M 39/1011; A61M 39/105; A61M 16/00; A61M 16/08; A61M 16/0875; A61M 16/10; A61M 16/14; A61M 16/20; A61M 2205/582; F16L 37/252
See application file for complete search history.

(56) References Cited

U.S. PATENT DOCUMENTS

| | | | | |
|---|---|---|---|---|
| 4,758,023 A | * | 7/1988 | Vermillion | F16L 37/252 285/401 |
| 4,951,661 A | * | 8/1990 | Sladek | A61M 16/0808 128/202.27 |
| 5,462,311 A | * | 10/1995 | Cipolla | A47L 9/244 285/24 |
| 5,479,920 A | * | 1/1996 | Piper | A61M 15/00 128/203.12 |
| 6,539,939 B2 | * | 4/2003 | Rubin | A61M 15/0086 128/200.23 |
| 6,578,571 B1 | * | 6/2003 | Watt | A61M 15/00 128/200.14 |
| 6,925,686 B2 | * | 8/2005 | Heathcock | B25G 1/04 15/144.4 |

(Continued)

*Primary Examiner* — Joseph D. Boecker
(74) *Attorney, Agent, or Firm* — Daniel S. Polley, P.A.

(57) ABSTRACT

A medical delivery device is disclosed having separate adaptors that are removably secured to the inlets of a manifold member through the use of mating locking mechanisms. The locking mechanisms allow the adaptors to be unsecured and switched, or other adaptors secured, which allows the same y-shaped member to increase its functional use to various different applications. Preferably, the delivery device comprises three separate pieces comprising a Y-shaped member having two inlets and an outlet, a first valve adaptor removably secured to one of the inlets and an angled shaped adaptor removably secured to the other inlet. As the two adaptors are removably secured to the Y-shaped member they can be unsecured and their resecurement switched. The mating locking mechanisms also aid in making sure that the adaptors are properly aligned with the inlets when secured thereto.

17 Claims, 7 Drawing Sheets

(56) References Cited

U.S. PATENT DOCUMENTS

| | | | | |
|---|---|---|---|---|
| 9,642,980 | B2* | 5/2017 | Alizoti | A61M 16/0816 |
| 2002/0162554 | A1* | 11/2002 | Loescher | A61M 16/00 |
| | | | | 128/204.18 |
| 2006/0231091 | A1* | 10/2006 | Camarillo | A61M 15/0086 |
| | | | | 128/200.21 |
| 2007/0240709 | A1* | 10/2007 | Woolley | A61M 16/08 |
| | | | | 128/200.21 |
| 2007/0283951 | A1* | 12/2007 | Burk | A61M 16/06 |
| | | | | 128/200.21 |
| 2008/0210242 | A1* | 9/2008 | Burk | A61M 16/06 |
| | | | | 128/206.21 |
| 2008/0264413 | A1* | 10/2008 | Doherty | A61M 16/021 |
| | | | | 128/202.27 |
| 2009/0312727 | A1* | 12/2009 | Heaton | A61M 1/008 |
| | | | | 604/318 |
| 2010/0024818 | A1* | 2/2010 | Stenzler | A61M 16/0463 |
| | | | | 128/204.18 |
| 2012/0272956 | A1* | 11/2012 | Rusher | A61M 16/208 |
| | | | | 128/203.12 |
| 2013/0126011 | A1* | 5/2013 | Abraham | F16K 13/00 |
| | | | | 137/315.01 |
| 2013/0199520 | A1* | 8/2013 | Dhuper | A61M 16/0816 |
| | | | | 128/200.23 |
| 2014/0137860 | A1* | 5/2014 | Lanier | A61M 16/0833 |
| | | | | 128/202.27 |
| 2015/0224278 | A1* | 8/2015 | Addington | A61M 16/147 |
| | | | | 128/200.21 |

\* cited by examiner

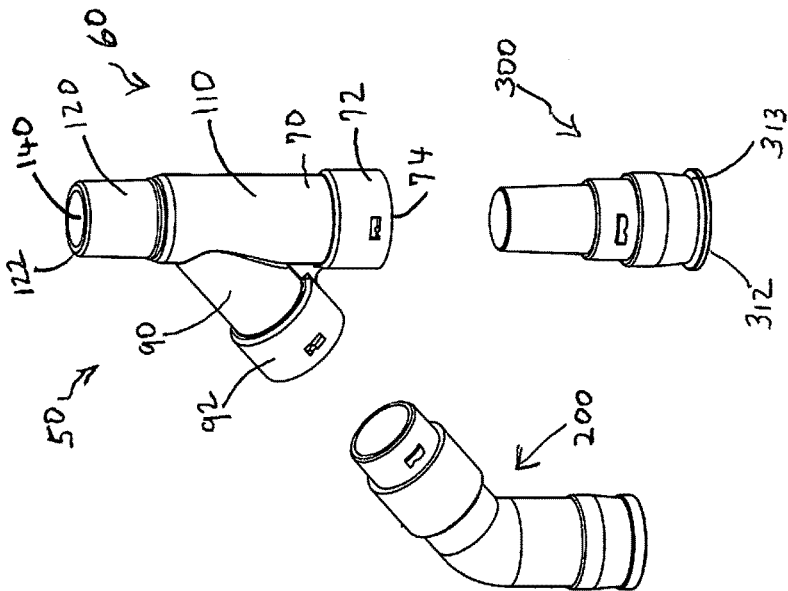
Figure 1
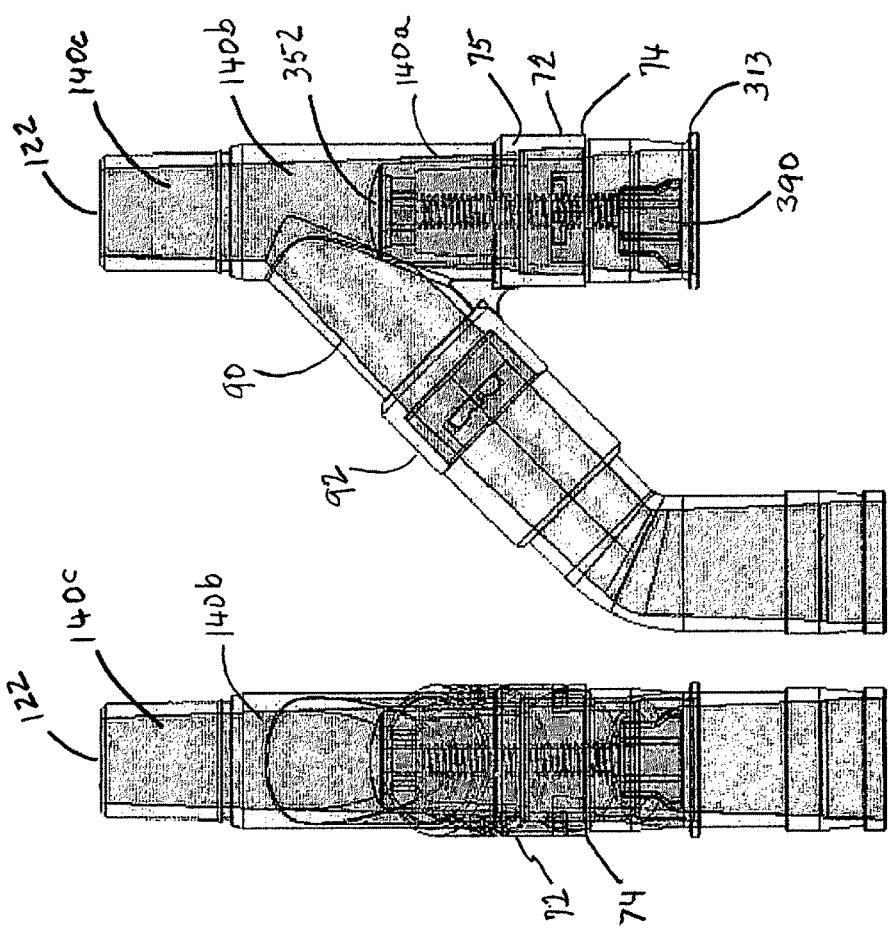
Figure 2
Figure 3

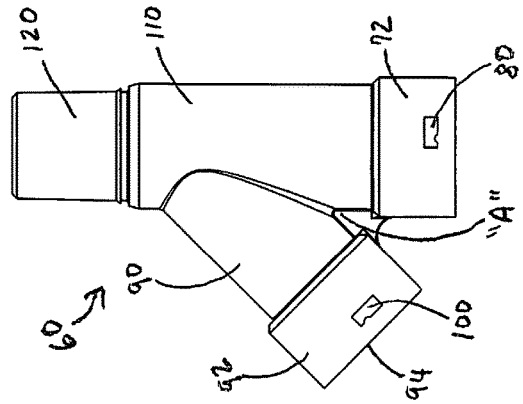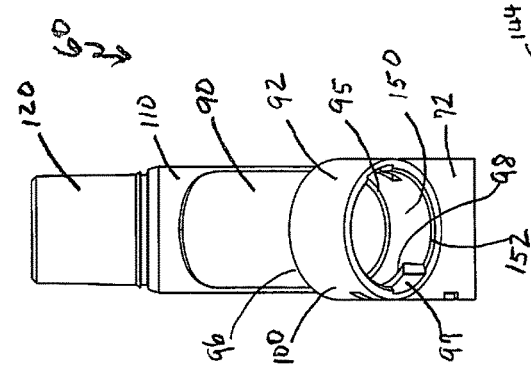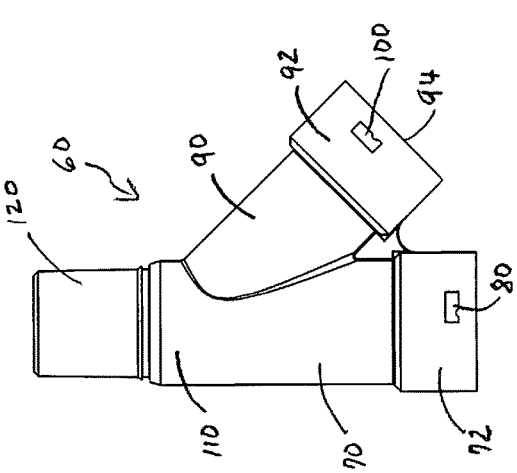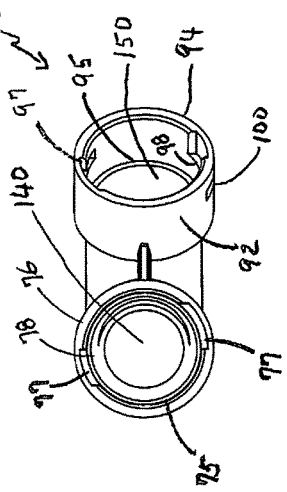

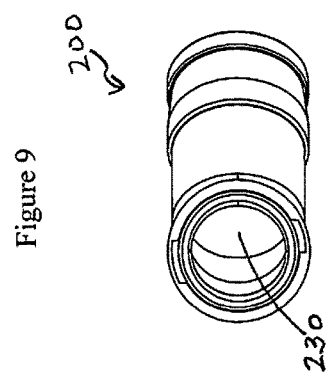
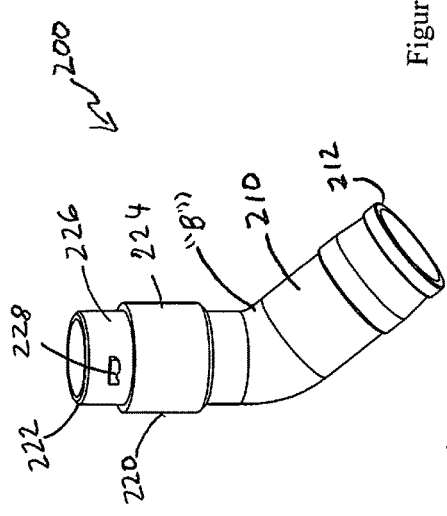
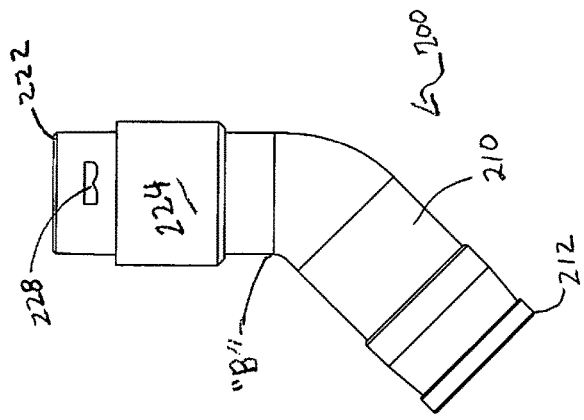
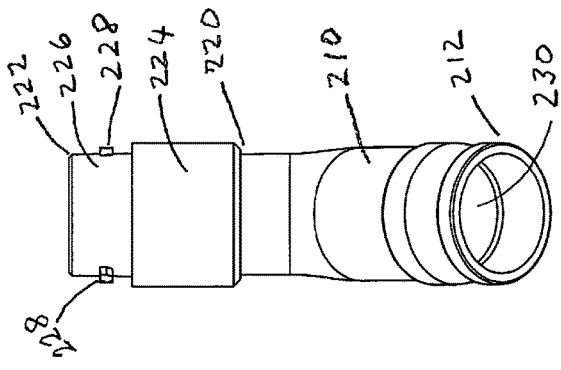
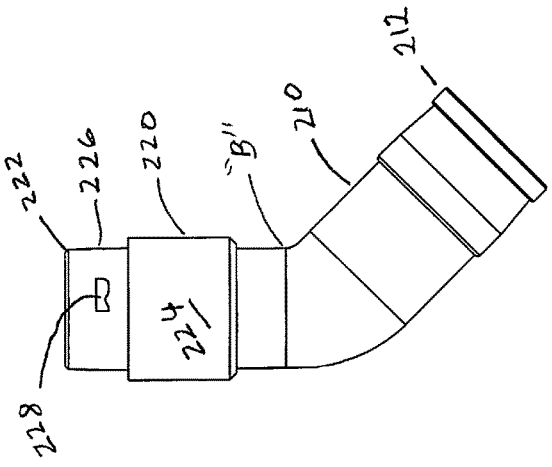
Figure 9
Figure 10
Figure 11
Figure 12
Figure 13

MULTI-FUNCTIONAL DEVICE HAVING AN INTERCHANGEABLE OPTION FOR A SPRING-LOADED VALVE FOR DELIVERING INHALING MEDICAL GAS AND/OR NEBULIZED MEDICINE TO A SPONTANEOUSLY BREATHING PATIENT

1. FIELD OF THE DISCLOSURE

The present invention relates generally to medical delivery devices and more particularly to devices for delivering inhaling medical gases and nebulized medicine to patients.

2. BACKGROUND

Nebulization and oxygen delivery systems are one of the most commonly performed procedures in the field of medicine, occurring in virtually every emergency room, general patient care areas in hospitals, long term care facilities, hospice, surgical services, ambulances, emergency medical services, animal clinics and even on the battlefield. Despite the frequency of using inhalation medical gases in combination with a nebulized therapy, due to the chronic disease or acute respiratory distress episode, due to hypoxemia and/or bronchoconstriction, patients continue to be compromised, because of the insufficient oxygen and/or medication being delivered to the patient during these critical changes.

Current devices for receiving separate inputs of inhaling medical gas and nebulized medicine, mixing such inputs and delivering the single mixed output of inhaling medical gas and nebulized medicine to a patient's breathing mask are provided as one-piece delivery devices. These one-piece devices are comprised of a Y-shaped member having two non-removable adaptor/port connectors permanently secured and/or monolithically formed with the inlets of the Y-shaped member. By permanently securing the adaptor/port connectors to the inlets, the delivery device is limited in its function and types of connections available to it.

The present disclosure is directed to overcoming the above-noted problems, as well as other problems, experienced with one-piece medical delivery devices.

SUMMARY OF THE DISCLOSURE

The present disclosure provided below describes a delivery device which greatly improves on these earlier one-piece devices by, amongst other improvements, providing separate independent adaptor/port connectors that are removably secured to the inlets of a y-shaped member through the use of locking mechanisms. The locking mechanisms allow the adaptors to be removed and switched (i.e. each is secured to the other inlet) and/or allow the adaptors to be replaced for one or more other types of adaptors (i.e. different size hoses or tubes, different functions, etc.). Thus, many different types of adaptors can be removably secured to the same y-shaped member, which allows the same y-shaped member to increase its functional use to various different applications.

Disclosed herein is a novel and unobvious multi-functional device which generally includes a Y-shaped member having two inlet conduits and an outlet, a first valve adaptor removably secured to one of the inlet conduits and an angled shaped adaptor removably secured to the other of the inlet conduits of the Y-shaped member. As the two adaptors are removably secured to the Y-shaped member they can be unsecured and their resecurement switched, such that the adaptors are secured to the inlet legs that they were not previously secured to. The ability for the delivery device to having several configurations allows the delivery device to be multi-functional.

Preferably, the Y-shaped member is one piece. Mating locking mechanisms for securing the adaptors to the inlet conduits can also be provided to help maintain the secured relationships, as well as aiding in making sure that the adaptors are properly aligned with the Y-shaped member.

Other type of adaptors that are provided with the same mating/locking mechanism can also be used with and removably secured to the Y-shaped member. Additionally, other shaped members with one or more inlets can also have the described removable locking mechanism incorporated into their designs, such that interchangeable adaptors can be secured to various shaped manifold members, in addition to the below-described y-shaped member, and such other shaped manifold members are also considered within the scope of the disclosure. Additionally, though described below with the inlets of the y-shaped member, it is also within the scope of the disclosure to incorporate that locking mechanism into an outlet of the y-shaped member (particularly where the outlet also is provided with a female receiving port—though not considered limiting) as well as one or more outlets of other shaped manifolds.

By removably securing the adaptors, the present invention provides for the novel feature of an interchangeable option for the spring-loaded valve adaptor.

Thus, discloses is a multifunctional, preferably disposable, single patient use delivery device that is preferably discarded after use. Non-limiting novel features of the above and below described delivery device include: (a) a singular tube and attached dog leg all with tapered ports; (b) a spring-loaded valve can only be opened manually and not by a forced medical gas; (c) maintains an "open system concept" due to the presence of the dog leg; (d) designed to be used for non-ventilated patients, where patient's spontaneous respiratory rate is required; (e) does not produce aerosolized medication and it does not make adjustments to the oxygen concentration and ensures delivery of the medication and medical gases at the various rates and concentrations; (f) capable of mixing different inhalation medical gases at the same time and ability to control precise percentage of the inhalation medical gas; (g) designed to be utilized with existing respiratory care equipment; and (h) can be used as a passageway, assembly or connector.

BRIEF DESCRIPTION OF THE DRAWINGS

FIG. 1 is an exploded perspective view of a preferred open system delivery device having three separate pieces comprising a preferred y-shaped member/manifold, angled adaptor and valve adaptor in accordance with the disclosure;

FIG. 2 is a first side elevational view of the delivery device of FIG. 1 and illustrating internal components of the preferred valve adaptor;

FIG. 3 is a second side elevational view of the delivery device of FIG. 2;

FIG. 4 is a first side elevational view of the y-shaped member/manifold of FIG. 1;

FIG. 5 is a second side elevational view of the y-shaped member/manifold of FIG. 1;

FIG. 6 is a third side elevational view of the y-shaped member/manifold of FIG. 1;

FIG. 6 is a bottom view of the y-shaped member/manifold of FIG. 1;

FIG. 8 is a perspective view of the y-shaped member/manifold of FIG. 1;

FIG. 9 is an end view of the angled adaptor of FIG. 1;

FIG. 10 is a perspective view of the angled adaptor of FIG. 1;

FIG. 11 is a first side elevational view of the angled adaptor of FIG. 1;

FIG. 12 is a second side elevational view of the angled adaptor of FIG. 1;

FIG. 13 is a third side elevational view of the angled adaptor of FIG. 1;

DETAILED DESCRIPTION OF THE EMBODIMENTS

Figure 15:
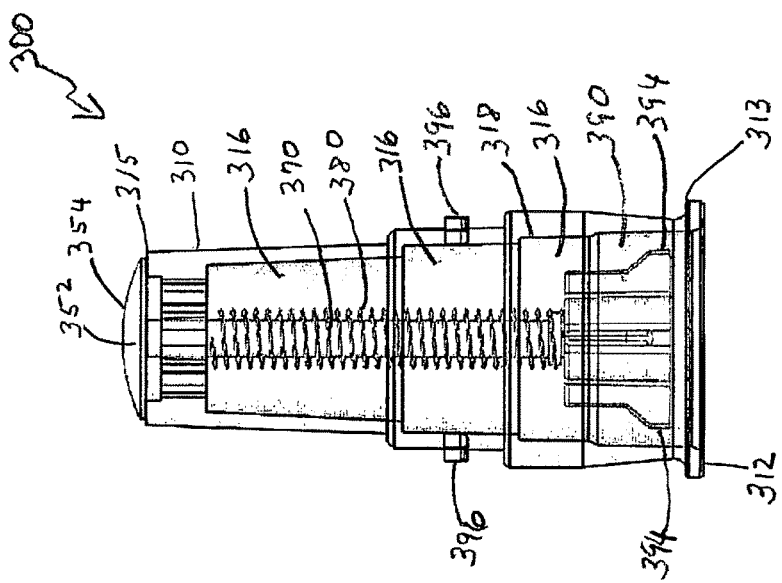
FIG. 15 is a side elevational view of the valve adaptor of FIG. 2.

As seen in the drawings figures a multi-function delivery device having multiple inlets and a single outlet for preferably delivering a combination of a source of oxygen or gas and a source of nebulized medicine to a patient is disclosed and generally designated as delivery device 50. As seen in FIGS. 1 and 2, in one non-limiting embodiment, delivery device 50 preferably comprises a generally Y-shaped member 60 serving as a manifold and having a first inlet conduit 70, a second inlet conduit 90, an intermediate middle member 110 and a single outlet conduit 120. First inlet conduit 70, second inlet conduit 90, intermediate middle member 110 and single outlet conduit 120 are monolithically formed or constructed integral to form a one-piece Y-shaped member 60. Delivery device 50 is not considered limited to Y-shaped member 60 and other shapes that allow for two inlets, a middle member for combining the contents from through the two inlets, and a single outlet for exiting the combined contents, while also having an appropriate size to allow it to be easily connected to a patient's mask, can also be used and is also considered within the scope of the disclosure. Additionally, other manifold shapes having one or more inlets and/or one or more outlets can also be incorporated with the removable securement embodiments described herein and are also considered within the scope of the disclosure.

Also seen in FIGS. 1 and 2, a female receiving port 72 is preferably monolithically formed at an outer end of the first inlet conduit 70 and a similar female receiving portion 92 is preferably monolithically formed at an outer end of the second inlet conduit 90. Middle member 110 is positioned between first inlet conduit 70 and single outlet conduit 120. A plurality of outlet conduits can also be used (where the combined contents is divided and routed to multiple sources) and are also considered within the scope of the disclosure, which could also result in delivery device 50 not being Y-shaped.

As seen in FIGS. 4 through 8, first inlet conduit 70, middle member 110 and single outlet conduit 120 are preferably coaxial and together collectively define a continuous first internal passageway 140 extending from an outer end 74 of first inlet conduit 70/female receiving port 72 to an outer end 122 of single outlet conduit 120. The area of first passageway 140 defined by first inlet 70 is designated as area 140a, while the area of first passageway 140 defined by middle member 110 is designated as area 140b and the area of first passageway 140 defined by single outlet conduit 120 is designated as area 140c. A first end 142 and a second end 144 of first internal passageway 140 are both preferably open.

Also seen in FIGS. 4 through 8, a second internal passageway 150 is defined by second inlet conduit 90 and extends from outer end 94 of second inlet conduit 90/female receiving port 92 to the opposite end of second inlet conduit 90 terminates into middle member 110. First end 152 of second internal passageway 150 is open and the opposite end of second internal passageway 150 is also open and terminates into and is in communication with first internal passageway 150. Thus, area 140b of first internal passageway preferably defines the internal area of delivery device 50 where the contents (e.g. oxygen, nebulized medicine, etc.) flowing through the first inlet conduit 70 and the contents (e.g. oxygen, nebulized medicine, etc.) flowing through the second inlet conduit 90 meet and are preferably combined, mixed, etc. as they jointly exit out of single outlet conduit 120 for delivery to the patient or other individual (i.e. through a mask, etc.).

The angle "A" between first inlet conduit 70 and second inlet conduit 90 (See FIGS. 4 and 6) can be acute and can be within the range of about 35° to about 55°. In a preferred embodiment, the angle selected can be about 45°, though such is not considered limiting and other higher or lower angles can be selected and are considered part of the disclosure.

As best seen in FIGS. 5 and 7, preferably, both female receiving port 72 and female receiving port 92 are provided with a securement mechanism for aligning and removably securing an adaptor to first inlet conduit 70 and second inlet conduit 90, respectively. Though not limiting, the securement mechanism is preferably the same for both receiving port 72 and female receiving port 92. As best seen in FIGS. 5 and 7, ports 72 and 92 are provided with a thickness 76/96 of material. Preferably, at two locations a portion of the internal surface of port 72/92 is removed (i.e. an internal cutout 77/97 is provided) which extends from first end 74/94 inward a certain distance, though preferably terminating at an intermediate point 78/98 of port 74/94, respectively. Though not considered limiting, the shape of cutout 77/97 can be rectangular or square in shape and preferably can be chosen based on the shape of protrusion(s) disposed on the adaptor(s) to be removably secured to one of the inlet conduits, which will be described in further detail below. Preferably, to one side of cutout 77/97, an aperture 80/100 is provided in port 74/94, respectively, for receipt of the protrusion(s), when an adaptor is removably secured to port 74 or 94. Preferably, aperture 80/100 can be rectangular or square in shape and is preferably chosen based on the shape of the protrusion. However, such is not considered limiting and aperture 80/100 can be shaped differently than a rectangular or square, as well as irregularly shaped, and such other shapes are also within the scope of the disclosure.

The inner diameter of the internal passageway associated with port 74 can be larger than the inner diameter of the internal passageway associated with the remainder of first inlet conduit 70 to create a step or ledge 75 where the two internal passageways meet (See FIG. 7). Similarly, the inner diameter of the internal passageway associated with port 94 can be larger than the inner diameter of the internal passageway associated with the remainder of the second inlet conduit 90 to create a step or ledge 95 where the two internal passageways meet.

As seen in FIGS. 4 and 6, the outer diameter of single outlet conduit 120 can be smaller in size than the outer diameter of the remaining portions of Y-shaped member 60 (i.e. first inlet conduit 70, second inlet conduit 90 and middle member 110), such that single outlet conduit 120 can be a male insertion member when securing Y-shaped member 60 to a female receiving portion of another object (i.e. mask worn by a patient, etc.).

Though not required or considered limiting, the inner surface of the internal passageways 140a and 150 associated with first inlet conduit 70 and second inlet conduit 90 can be tapered inwardly (inner diameter is reduced as you move inside the passageways) to assist in the connection of the first and second inlet conduits to the insertion ends of one or more adaptors (discussed in more detail below), as well as other tubes, hoses, etc. (See FIGS. 2, 3 and 7). Similarly and again not required, the outer diameter of single outlet conduit 120 can increase as one moves from its outer end towards middle member 110 to assist in the connection of outlet conduit 120 to another object, such as, but not limited to a patient's mask.

A first adaptor for use with delivery device 50 is best seen in FIGS. 9 through 13 and generally designated as adaptor 200 having a first portion 210 with an outer end 212 and a second portion 220 with an outer end 222. Preferably, first adaptor 200 is a one-piece member and first portion 210 and second portion 220 are monolithically formed together to form first adaptor 200. Adaptor 200 can be considered an elbow adaptor as first portion 210 is preferably at an angle with respect to second portion 220. The angle "B" between the two portions is preferably obtuse and can range from about 125° to about 145°. (See FIGS. 10, 11 and 13) In one non-limiting embodiment, angle B can be about 135°. An internal passageway 230 through adaptor 200 is defined by first portion 210 and second portion 220 and extends from outer end 212 (which can be considered the inlet end of adaptor) to outer end 222 (which can be considered the outlet end of adaptor 200). An intermediate area 224 of second portion 220 can be extended in outer diameter as compared to the remaining areas of second portion 220. An area 226 of second portion 220 closest to outer end 222 can have a protrusion 228 extending upward from its outer surface. Protrusion 228 can be preferably shaped to correspond to the shape of aperture 80 and/or aperture 100. When securing first adaptor 200 to first inlet conduit 70, to ensure proper alignment and securement, outlet/insertion end 222 of adaptor 200 is inserted into receiving port 74 by aligning protrusion 228 with cutout 77 and pushing adaptor 200 inward. Once protrusion 228 preferably reaches the end of cutout 77, twisting adaptor 200 to the right will cause protrusion 228 to be received within aperture 80. The location of the cutout 77 and aperture 80 to each other can be switched and in such case, adaptor 200 is preferably switched to the left for protrusion 228 to be received within aperture 80. Based on the tight relationship dimensions of area 226 with respect to the inner diameter of receiving port 74, portion 220 preferably can only be inserted into port 74 by aligning protrusion 228 with cutout 77. Once protrusion 228 is received within aperture 80 (and locked in position/securement), preferably the only way to remove protrusion 228 from aperture 80 (to release the securement of adaptor 200 to first inlet conduit 70) is to twist adaptor 200 to the left (if adaptor 200 was initially twisted to the right to have protrusion 228 be received within aperture 80 and the opposite if adaptor was initially twisted to the left for securing adaptor 200 to first inlet conduit 70) which causes protrusion 228 to be located within the cutout 77 and permits area 226 of portion 220 to be pulled out of receiving port 74.

The securement of adaptor 200 to first inlet conduit 70 was discussed above through a single protrusion 228, cutout 77 and aperture 80. Preferably, area 226 is provided with two protrusions 228 and receiving port 74 is provided with two cutouts 77 and two apertures 80. (See FIGS. 5 and 7). Preferably, by aligning one of the protrusions 228 with one of the cutouts 77 can automatically also align the second protrusion 228 with the outer (second) cutout 77. As such, twisting the adaptor 200 can cause both protrusions 228 to be received within corresponding apertures 80 at virtually the same time. Preferably, the spacing of protrusions 228 on area 226 is such that they are opposite to each other, and similarly, the spacing of cutouts 77 and apertures 80 on receiving port 74 are also opposite to each other, though such is not considered limiting other spacings for the protrusions, cutouts and apertures can be incorporated into the design and are considered within the scope of the disclosure. With two protrusions, cutouts and apertures, two attachment positions are provided for adaptor 200 with respect to Y-shaped member 60. It is also within the scope of the disclosure to incorporate three or more protrusions, cutouts and apertures, which will also increase the number of attachment positions.

Adaptor 200 can also be similarly removably secured to second inlet conduit 90 (FIGS. 1 through 3), through similarly aligning protrusion(s) 228 with cutout(s) 97 and twisting adaptor 200 (to the right or left as described above) to cause the protrusion(s) 228 to be receiving within aperture(s) 100. The dimensions, location and relationship between cutouts 97 and apertures 100 to each other, as well as the number of cutouts 97 and apertures 100 provided for receiving port 94, can be the same as described above for cutouts 77 and apertures 100 of first inlet conduit 70. Also similar to the above, with preferably more than one cutout and aperture, adaptor 200 can be removably secured to second inlet conduit 90 in a plurality of positions.

Figure 14:
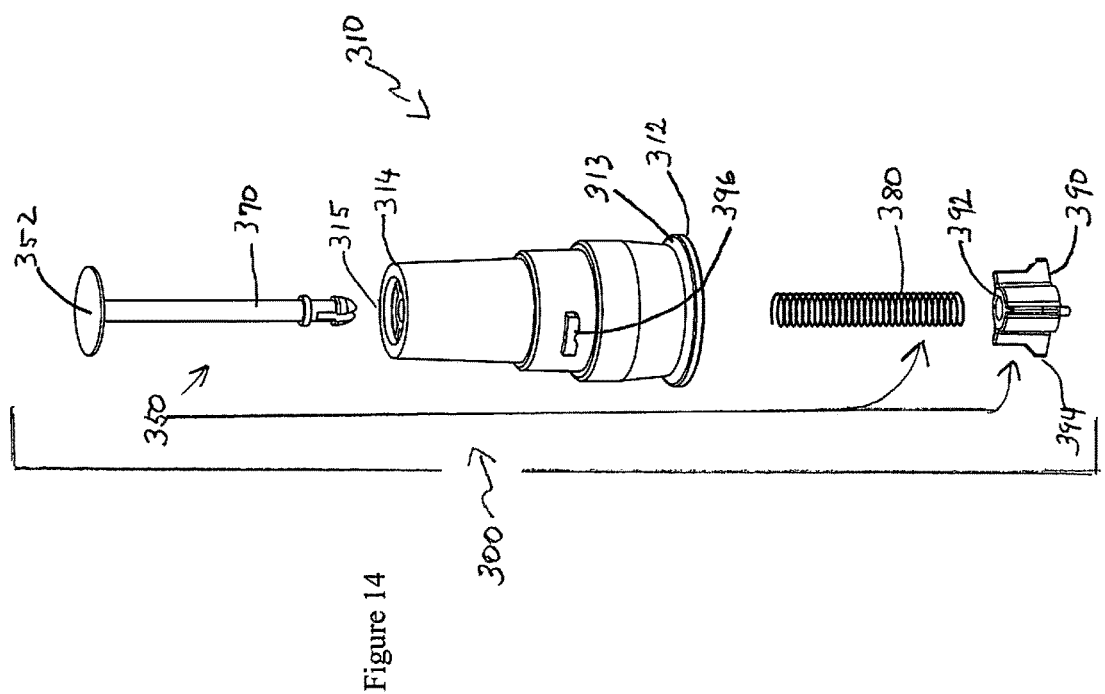
FIG. 14 is an exploded perspective view of the valve adaptor of FIG. 1.
Figure 17:
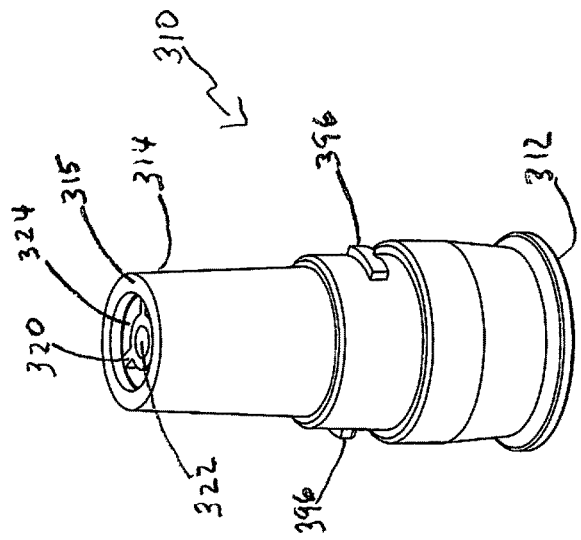
FIG. 17 is a perspective view of the valve housing of the valve adaptor of FIG. 1.
Figure 16:
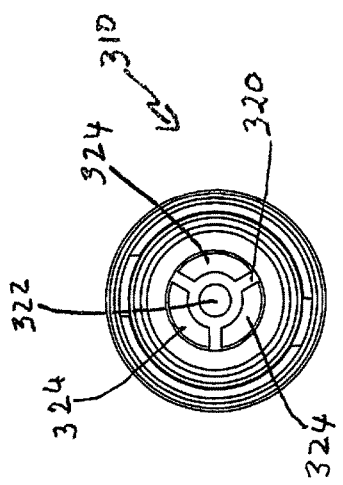
FIG. 16 is a bottom view of the valve housing of the valve adaptor of FIG. 1.

A valve adaptor 300 (best seen in FIGS. 14 to 25 and preferably spring loaded/loading) can also be similarly removably secured to either first inlet conduit 70 and/or second inlet conduit 90. Valve adaptor 300 includes a housing 310 having an inlet end 312 and an outlet end 314 and an internal passageway 316 extending from inlet end 312 to outlet end 314. Outlet end 314 is provided with an external ledge 315. The inner diameter of internal passageway 316 at inlet end 312 can be larger than the inner diameter of internal passageway 316 at outlet end 312. This allows for an internal step or ledge 318 to be disposed within internal passageway preferably closer to inlet end 312, as compared to outlet end 314. As seen in FIG. 17, housing 310 also has an internal positioning member 320 located within internal passageway 316 preferably near outlet end 314, though such is not considered limiting and positioning member 320 can be located at other locations within internal passageway 316. Positioning member 320 can be provided within a center aperture 322 and one or more, and preferably a plurality of, perimeter apertures 324. As seen in FIG. 14, valve adaptor 300 also includes a valve member 350 generally comprised of a sealing cap 352, valve stem 370, spring 380 and stop member 390. Sealing cap 352 can have a slightly rounded outer surface 354 and a flat bottom surface 356. Outer surface 354 can also be flat in shape which is also considered within the scope of the disclosure. The outer diameter of cap 352 is preferably the same or almost the same as the outer diameter of housing 310 at outlet end 314, such that when cap 352 is in a closed/sealing position it preferably does not extend beyond outer surface of the elongated housing 310. The outer diameter of cap 352 is larger than the inner diameter of passageway 316 at outlet end 314, such that in the closed/sealing position, bottom surface 356 of cap 352 rests against external ledge 315 at outlet end 314 and cap 352 does not enter into internal passageway 316.

Valve stem 370 is secured to cap 352 at one end and to stop member 390 at its opposite end 373 (See FIG. 15). In one non-limiting embodiment for securing valve stem 370 to stop member 390, stop member can be provided with an aperture, such a central aperture 391 preferably surrounded by an inner bottom surface 397, preferably located within a body or housing portion of stop member 390 (See FIGS. 22 through 25). End 373 that is secured to stop member 390 can be provided with one or more, and preferably two, prongs 375 with each prong 375 having an upper contact surface 377 (See FIGS. 19 and 20). To secure valve stem 370 to stop member 390, prongs 375 are squeezed inward and inserted through aperture 391. Once through aperture 391, prongs 375 rebound outward such that upper contact surface 377 of each prong 375 contacts or is adjacent to a portion of inner bottom surface 397 and prongs 375 preferably cannot be easily and inadvertently pulled back through 391 (i.e. thus locking/securing end 373 of valve stem 370 to stop member 390).

As seen in FIG. 15, spring 380 is secured around at least a portion of valve stem 370. When securing valve member 350 to housing 310, valve stem 370 is inserted through center aperture 322 of positioning member 320 to help maintain valve member 350 in proper position with respect to valve housing 310, The diameter of spring 380 is larger than the diameter of center aperture 322, such that spring 380 is maintained in position along a portion of valve stem 370 between positioning member 320 and a top surface 392 of stop member 390. Stop member 390 is also provided with at least one, and preferably a plurality of flange portions 394 that extend outward within the portion of internal passageway 316 associated with inlet end 312 (the largest diameter section 316a of passageway 316). The outer diameter of stop member 390 at the flange portions is larger than the inner diameter of the passageway section 316b adjacent section 316a, which prevents the plurality of flange portions 394 from being movable into passageway section 316b, as the flange portions 394 come into contact with inner step or ledge 318 and defines how far stop member 390 can travel within passageway 316, which in turns also defines how far cap 352 moves away from outlet end 314 of valve adaptor 300 when medicine, gas, fluids, etc. are travelling within passageway 316 at enough pressure, force, speed, etc. to overcome the tension/expansion force of spring 380 (valve "open" position). When no medicine, gas, fluid, etc. is traveling through passageway 316 or at a pressure, force, speed, etc. that is not sufficient to overcome the tension/expansion force of spring 380, the expansion spring 380 will move and maintain stop member 390 towards inlet end 312 of valve adaptor 300 (valve "closed" position). Spring 380 preferably automatically returns cap 352 to its resting spot on external ledge 315 (from a valve "open" position to a valve "close" position) whenever there is not a sufficient of force, pressure, speed, etc. of content (e.g. gas, medicine, etc.) traveling through passageway 316 or no content (i.e. no force, pressure, etc.).

As seen in FIGS. 15 and 17, a portion of the outer surface of housing 310 defining internal passageway portion 316b can be provide with protrusion(s) 396 which is (are) used to secure valve adaptor 300 to either first inlet conduit 70 and/or second inlet conduit 90 similar to the description of attaching adaptor 200 to first inlet conduit 70 or second inlet conduit through the use of protrusion(s) 228 and the description above is incorporated by reference. It is also within the scope of the disclosure to provide protrusion(s) 396 at other points of the outer surface of adaptor valve housing 310, which may result of the length of valve housing to be extended. Preferably, the outlet of valve adaptor 300, when properly secured to either inlet of y-shaped member 60, is positioned such that the content traveling through adaptor 300 empties into middle member 110 for mixing with the content from the other inlet of y-shaped member.

Thus, as described above, in the preferred embodiment an open system is provided as the delivery device comprises three separate pieces or parts, namely, y-shaped member 60, removably secured adaptor 200 and removably secured valve adaptor 300. In one embodiment y-shaped member 60, adaptor 200 and housing 310 of valve adaptor 300 can be constructed from a plastic material and preferably from the same plastic material, though such is not considered limiting and other materials can be used and the various parts do not have to be constructed from the same material. Preferably, the material selected for y-shaped member 60, adaptor 200 and valve adaptor 300 is a FDA approved material for medical devices.

It is also preferred that the material selected be clear, transparent or translucent for at least valve adaptor 300 and preferably y-shaped member 60, angled adaptor 200 and valve adaptor 300. With the clear material the inside of delivery device 50 can be viewed. Valve cap 352, valve stem 370 and/or stop member 390 can be constructed from a dark material or darkened, in order to provide contrast (between these parts and valve adaptor housing 310) so that the spring loaded/loading valve can be viewed by the user, hospital staff, another individual, etc. Thus, the movement of these darkened parts during use allows for confirmation that they are properly operating and to see the exact location of these parts within valve adaptor housing 310 without having to disassemble delivery device 50 or adaptor valve 300.

The various receiving ports can be tapered to aid in securement of the object being attached thereto.

Accordingly, in one use the delivery device described herein allows for separate inlet supplies (e.g. gas/oxygen and nebulized medicine) to be separately received by the delivery device, mixed within the delivery device and delivered to the patient's mask through a single outlet. As the adaptors are no longer permanently secured to the manifold (i.e. y-shaped member) and thus interchangeable, various set up configurations can be used with adaptors 200 and 300, including securing adaptor 200 in a plurality of different orientations, and switching the inlets for which each adaptor is removably secured to. Also, the removable adaptor capabilities also allows for two adaptors 200 to be removably secured or two adaptors 300 to be removably secured to y-shaped member 60. Additionally, other types and/or sizes of adaptors, if provided within the same locking mechanism as provided for adaptor 200 and/or adaptor 300, can also be removably secured to the same y-shaped member 60. Therefore, a single y-shaped member 60 is now provided with multiple and potentially endless functional uses previously not available with one-piece delivery devices.

Figure 18:
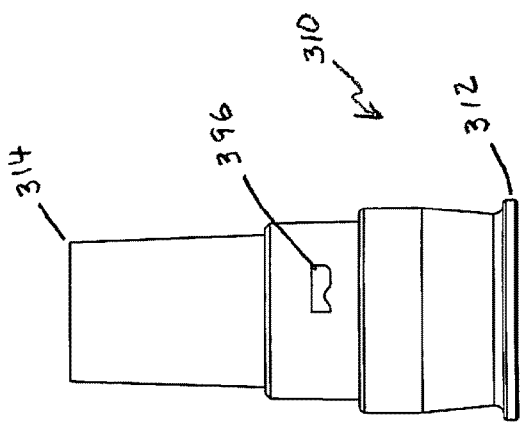
FIG. 18 is a side elevational view of the valve housing of the valve adaptor of FIG. 1.
Figure 20:
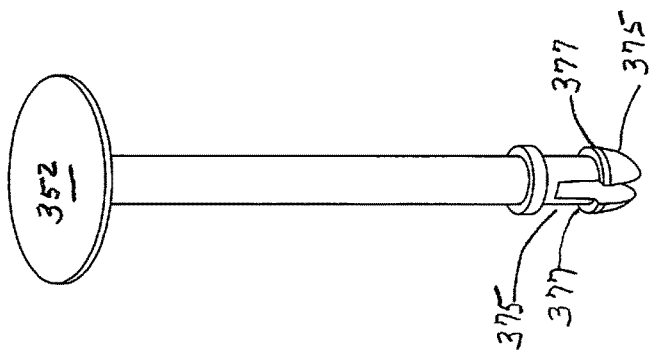
FIG. 20 is a perspective view of the valve cap and valve stem of the valve adaptor of FIG. 1.
Figure 19:
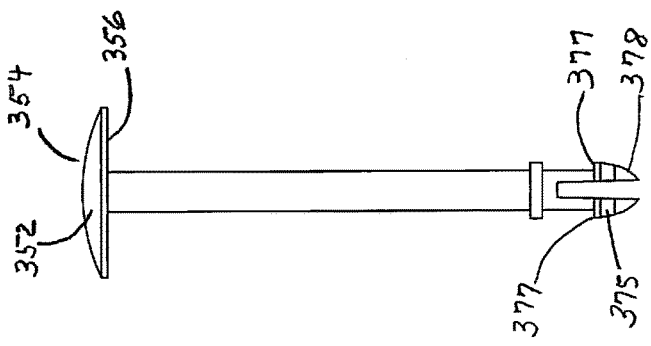
FIG. 19 is a side elevational view of the valve cap and valve stem of the valve adaptor of FIG. 1.
Figure 21:
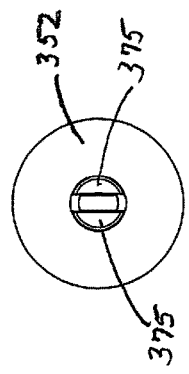
FIG. 21 is a bottom view of the valve cap and valve stem of the valve adaptor of FIG. 1.
Figure 24:
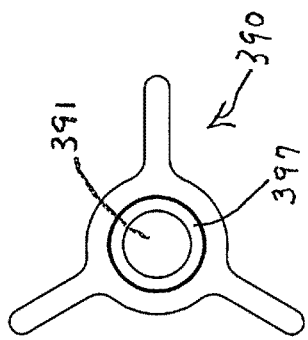
FIG. 24 is a bottom view of the stop member of the valve adaptor of FIG. 1.
Figure 23:
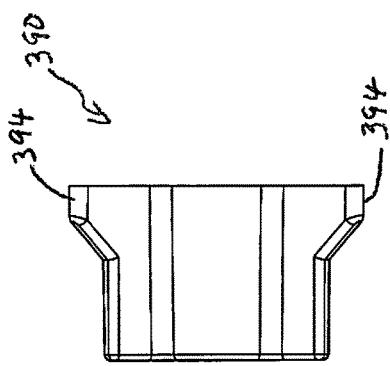
FIG. 23 is a side elevational view of the stop member of the valve adaptor of FIG. 1.
Figure 25:
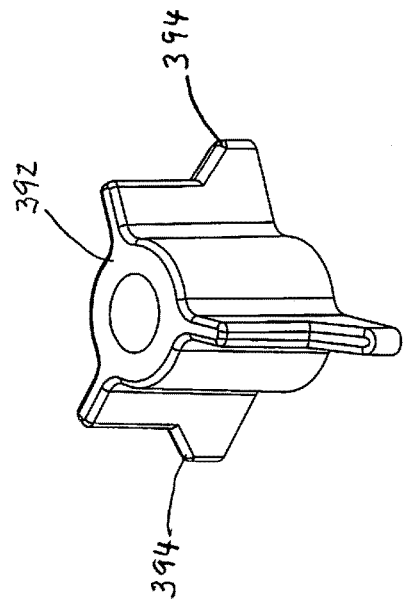
FIG. 25 is a perspective view of the stop member of the valve adaptor of FIG. 1.
Figure 22:
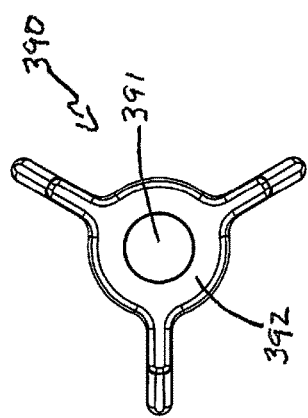
FIG. 22 is a top view of the stop member of the valve adaptor of FIG. 1.

As best seen in FIGS. 14 and 18, a safety ring 313 can be provided at inlet end 312. Safety ring 313 is preferably provided and extends the outer diameter at inlet end 312 of the spring loaded valve adaptor 300. Safety ring 313 protects the patient as it prevents medical personal from inadvertently applying or securing corrugated oxygen tubing to inlet end 312. By enlarging the outer diameter at inlet end 312, the corrugated oxygen tubing is blocked from being able to be secured to adaptor 300. This can be important where the pin of the spring-loaded valve of adaptor 300 can only be activated (i.e. moved to open position, etc.) manually and not by a force of medical gas. In such situations, if the corrugated oxygen tubing was accidentally secured at inlet end 312, the delivery of the medical gas to the patient would be block by the valve unable to move from its closed position, thus, resulting, in the patient's oxygen demand being compromised. As the corrugated oxygen tubing preferably cannot be secured to adaptor 300 in view of safety ring 313, the medical personnel is forced to secure the tubing to the inlet end of angled (i.e. dog leg) adaptor 200, where there preferably is no valve, barrier or any other obstruction which could affect the delivery of the medical gas to the patient, thus allowing the medical gas to reach the patient without any problem.

Delivery device 50 can be used with various equipment, including various types of medical equipment, such as, but not limited to, masks, venture devices, nebulizers, dual nebulizers, mouthpieces, rebreathers, partial rebreathers, gas or oxygen reservoir bags, tracheostomy collars/masks, cool aerosol devices, tubing, corrugated tubing, face tents, infant masks, pediatric masks, adult masks, etc.

Using delivery device 50 can provide a patient an inhalational medical gas comprising essentially 100% oxygen at a medically-appropriate flow-rate, while also providing and entraining a flow of a nebulized medicine within the flow of oxygen. Thus, a first stream of oxygen at a medically-appropriate flow-rate can be provided through adaptor 200, while a second stream of oxygen at a reduced flow-rate appropriate to nebulize a medicine can be provided through adaptor 300. The first and second streams are then combined into a single stream of inhalational medical gas and exited out to the patient.

Delivery device 50 can be preferably suitable to interface with various types of patient masks, including, but not limited to, conventional patient masks found in a hospital. The single outlet of delivery device 50 can be preferably configured/constructed such that it can be adapted to fit an inlet port of patient masks such as, but not limited to, neonatal masks, infant masks, pediatric masks, juvenile masks, face tents, tracheostomy collars/mask and adult masks.

Through the use of interchangeable and removable adaptors that can be secured to the first inlet 70 and second inlet 90 of y-shaped member 60, a single delivery device 50 can be provided and suitable for interfacing with various sources of inhalational medical gas found at an hospital. The inlet port of adaptor 200 and/or adaptor 300 can be preferably configured such that it can be adapted to fit the exit port of gas sources such as, but not limited to, oxygen hoses and nebulized medicine hoses As a non-limiting example, delivery device 50 allows for combining a primary oxygen stream with a stream of oxygen containing a nebulized medicine and exiting the combined mixture out of a single outlet. Valve adaptor 300 can be provided with an inlet port that can be adapted to interface with various types of inhalational medical gas and/or nebulized medicine sources typically found in a hospital. The valve aspect of adaptor 300 can provide for a gas-tight valve. The valve is adapted such that when the adaptor 300 is connected to a source of inhalational medical gas/nebulized medicine, the valve can automatically move to an open position to admit the passage of gas/medicine. When the combined gas/medicine source is not connected to the inlet of valve adaptor 300, the valve is automatically disposed in a closed position and does not permit the passage of gas into y-shaped member 60.

Often, a patient under medical care may have need of both inhalational oxygen at high concentrations and a high flow rates and also of nebulized medicine. Gas flow rates required to appropriately nebulize a medicine are often too low to provide medically-appropriate oxygenation to a patient. As one non-limiting example, depending on a patient's medical condition, oxygen flow rates of at least 15 liters per minute may be required. However, to nebulize various medications lower flow rates of about 6 to about 8 liters per minute may be required. Doctors are often faced with a dilemma of either providing appropriate oxygenation in the absence of medication, or of providing medication, but at a flow rate that provides insufficient oxygenation. The disclosed novel three-piece delivery device 50 (i.e. y-shaped member 60, adaptor 200 and valve adaptor 300) permits for simultaneously providing to the patient appropriate levels of both oxygen and medication.

Additionally, both patient masks and inhalational medical gas supplies may have different sized fittings necessitating stocking a variety of adaptors. The disclosed delivery device 50 allows for securing adaptors having various inlet sizes, allowing a single delivery device 50 to interface with various masks and gas supplies that are found in a hospital.

The disclosed novel delivery device 50 provides for a method to treat a patient with high flow rates of inhalational oxygen together with a flow of nebulized medicine. Preferably, the supply of medical oxygen is attached to the inlet of angled adaptor 200. The supply may be directly from a tank or may be via intermediary devices. When angled adaptor 200 is removably secured to first inlet 70 of y-shaped member 60, adaptor 200 directs the flow of oxygen to first inlet 70 and into intermediate member 110. The flow of oxygen can be considered a first stream of inhalational medical gas. Valve adaptor 300 can be removably secured to second inlet 90 of y-shaped member 60. A second stream of inhalational medical gas may be attached to the inlet of valve adaptor 300. Valve adaptor 300 is preferably fitted with a valve means such that, in the absence of a second stream of inhalational medical gas, the valve can be closed thus prohibiting the first stream (oxygen) from exiting out of y-shaped member 60 through second inlet 90 away from the patient, instead of correctly through outlet 120. A stream of nebulized medicine (second inhalational medical gas stream) may be coupled to the inlet of valve adaptor 300. The second stream may be provided directly from a nebulizer. Alternatively, the second stream may be provided via one or more intermediary devices. The second stream may comprise a medicine nebulized in a stream of medical oxygen. The flow rate of the second stream may be less than the flow rate of the first stream.

Other non-limiting examples of uses or application for the delivery device 50 include:

(1) for acutely ill patients, who require high oxygen concentration, providing double minute ventilation with high flow oxygen by applying double reservoir bags to meet higher patient's oxygen demand and higher minute ventilation volume;

(2) for chronically ill patients, who don't require high oxygen concentration, mixing low and precise percentage of oxygen, like 24% FiO2, provided by a venti-mask and giving nebulized therapy to the patient via an air compressor while not compromising the patient's CO2 drive. It will help to reduce, if not prevent, COPD patients from a condition known as a suppressed hypoxic drive and saves patients from being placed on a ventilator;

(3) for Status Asthmaticus patients, providing double nebulization cups to deliver double the amount of medication within a shorter period of time;

(4) for an open stoma or tracheostomy patients with T-Collar Masks, who require to use Cooling or Heated oxygenation and humidification, using delivery device 50 will help to provide simultaneous respiratory treatments without interrupting oxygenation and humidification;

(5) for post-op patients with facial surgery requiring face tents, the use of delivery device 50 can be beneficial as it can fit into the corrugated flexible tubing and other devices;

(6).

Certain benefits and advantages of delivery device 50 include, but are not limited to the following:

(1) Can use dual non-rebreathers and rebreathers masks;

(2) Can use dual nebulizers;

(3) Can adapt to cool and heated aerosol delivery systems with presided FiO2;

(4) Can adaptor to venti-masks, simple oxygen masks, face tents, tracheostomy collars and corrugated tubing;

(5) Can adapt to a neonatal, pediatric and adult oxygen masks;

(6) Provides for several safety features, including, but not limited to, tapered (receiving) ports, security mechanism, safety ring, manually open spring-loaded valve, open system concept, minimum number of moving parts, multifunctional, simplicity, uniqueness and versatility;

(7) Replaces Neb-U-Mask systems;

(8) Replaces Tee Adaptors without spring-loaded valve in most cases;

(9) In certain situations replaces Tee Adaptors with spring-loaded valve on non-ventilated patients;

(10) Reduces costs in view of simplicity, versatility and ability to perform multiple tasks at the same time and limits the amount of equipment needed to be purchased;

(11) Advanced spring-loaded valve with interchangeable option, safety ring and contrast (color coded, translucent in reference to black pin of the spring-loaded valve)

(12) Simultaneously deliver high flow medical inhalation gas (usually oxygen via non-rebreather or rebreather bag though not limiting) and nebulized therapy at the same time;

(13) Simultaneously deliver two nebulized therapies at the same time using either with air or oxygen;

(14) Simultaneously deliver two high inhalation medical gases at the same time (usually oxygen via dual non-rebreather bags and/or helium with a usual concentration 70/30 or 80/20 though not limiting);

(15) Simultaneously deliver low flow with a precised concentration of inhalation medical gas (usually oxygen via venturi-mask though not limiting) and nebulized therapy at the same time;

(16) Delivery device 50 can continue to be used even if one of the therapies is discontinued (usually at the spring-loaded attachment though not considered limiting).

Y-shaped member 60 serves as a manifold. The entrained first and second streams meet and can be mixed together at intermediate area 110 of y-shaped member 60 and preferably exit as a combined mixture out of outlet 120 for delivery to the patient. Thus, the first stream of inhalational medical gas and/or the entrained and combined first and second streams are directed through the exit outlet port 120 to the patient. As may be medically indicated, one or more devices may be disposed between the y-shaped member outlet 120 and the patient.

Accordingly, the disclosure provides for a novel delivery device that can be multi-functional, can be for a single patient use, can be disposable, can be a latex-free adaptor and can be discarded after use. The disclosed delivery device can be utilized with existing technology, and provides for an "an open system concept", that can deliver medical gases (e.g. air, oxygen, helium, etc.) and/or deliver nebulized medicine to the patient at various rates and concentrations.

Major types of accessories that can be used in conjunction with delivery device 50 include, without limitation, many of the accessories employed in the delivery of oxygen therapy. Non-limiting examples of specific products include simple oxygen masks, non re-breather masks, aerosol delivery systems, venturi oxygen delivery systems, as well most forms of pediatric and neo-natal aerosol delivery systems.

Delivery device can be used with existing respiratory medications, including Mucomyst, without having to be concern with stick valves issues. At the same time delivery device 50 can deliver and mix different medical gases, such as, but not limited to, air, oxygen and helium.

All components of the present disclosure delivery device having removably secured adaptors and their attachment locations, materials, sizes, shapes, attachment mechanisms, types of inlet gases and content, types of objects (e.g. hoses, tubes, masks, etc.) secured to the receiving ports and/or outlet, etc. discussed above or shown in the drawings, if any, are merely by way of example and are not considered limiting and other component(s) and their attachment locations, materials, sizes, shapes, attachment mechanisms, types of inlet gases and content, types of objects (e.g. hoses, tubes, masks, etc.) secured to the receiving ports and/or outlet, etc. currently known and/or later developed can also be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed, whether during prosecution of this application or in litigation or similar proceeding. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related or could be attributed to the function of the "means for" language.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A multiple pieces delivery device for mixing a plurality of separately received content and delivering the mixed content to a single outlet, comprising:
   a manifold member having a first inlet, a second inlet, an intermediate member and the single outlet, wherein the first inlet in internal communication with the intermediate member and the second inlet separately in internal communication with the intermediate member, wherein the first inlet and the second inlet are isolated from each other before being in communication at the intermediate member, said outlet in internal communication with the intermediate member;
   a first angled adaptor removably secured to either the first inlet or the second inlet of the manifold member, the first angle adaptor can be removably secured to the first inlet in a plurality of different orientations with respect to the manifold member and can be removably secured to the second inlet in a plurality of different orientations with respect to the manifold member, and
   a second valve adaptor removably secured to either the second inlet or the first inlet of the manifold member;
   wherein a first content is configured to travel through said first angled adaptor and ultimately received within the intermediate member and a second content is configured to travel through said second valve adaptor and ultimately received within the intermediate member and mixed with the first content wherein a mixture of the first content and the second content is configured to enter the outlet from the intermediate member;
   wherein the first inlet having an opening at an outer edge and a side wall defining an adaptor receiving area beginning at the outer edge of the first inlet and extending within the first inlet, the side wall of the first inlet having a plurality of apertures that are separate from the opening at the outer edge of the first inlet and allow the first angled adaptor or the second valve adaptor to be removably secured to the first inlet and allow the first angled adaptor to be removably secured at the first inlet in a plurality of orientations with respect to the manifold member; and
   wherein the second inlet having an opening at an outer edge and a side wall defining an adaptor receiving area beginning at the outer edge of the second inlet and extending within the second inlet, the side wall of the second inlet having a plurality of apertures that are separate from the opening at the outer edge of the second inlet and allow the first angled adaptor or the second valve adaptor to be removably secured to the second inlet and allow the first angled adaptor to be removably secured at the second inlet in a plurality of orientations with respect to the manifold member;
   wherein multiple securement orientations and locations of the first angled adaptor and the second valve adaptor to the manifold member allow for at least four separate content delivery positions for the first angled adaptor and second valve adaptor with respect to the manifold member to accommodate varying physical positions or a medical condition of a user of the multiple piece delivery device.

2. The multiple pieces delivery device of claim 1 wherein said first angled adaptor having a plurality of outer protrusions and said second valve adaptor having a plurality of outer protrusions;
   wherein said first angled adaptor is removably secured to the first inlet in one of a plurality orientations through the mating of the plurality of outer protrusions of said first angled adaptor with the plurality of apertures of the first inlet or said first angled adaptor is removably secured to the second inlet in one of a plurality orientations through the mating of the plurality of outer protrusions of said first angled adaptor with the plurality of apertures of the second inlet;
   wherein said second valve adaptor is removably secured to the first inlet through the mating of the plurality of outer protrusions of said second valve adaptor with the plurality of apertures of the first inlet or said second valve adaptor is removably secured to the second inlet through the mating of the plurality of outer protrusions of said second valve adaptor with the plurality of apertures of the second inlet.

3. The multiple pieces delivery device of claim 2 wherein the first inlet having two apertures and the second inlet having two apertures; wherein first angled adaptor having two outer protrusions and the second valve adaptor having two outer protrusions.

4. The multiple pieces delivery device of claim 3 wherein the first inlet having two internal cutouts and the second inlet having two internal cutouts.

5. The multiple pieces delivery device of claim 1 wherein the manifold member is
   a y-shaped manifold member with the first inlet disposed at a non-perpendicular angle with respect to the second inlet and the second inlet and outlet collinear with each other.

6. The delivery device of claim 5 wherein the side wall of the first inlet having a plurality of internal cutouts with each cutout extending from the outer edge of the first inlet up to an intermediate point of the first inlet;
   wherein each of the plurality of internal cutouts of the first inlet located adjacent to a side of one aperture of the plurality of apertures of the first inlet;
   wherein the side wall of the second inlet having a plurality of internal cutouts with each cutout extending from the outer edge of the second inlet up to an intermediate point of the second inlet;
   wherein each of the plurality of internal cutouts of the second inlet located adjacent to a side of one aperture of the plurality of apertures of the second inlet.

7. The delivery device of claim 6;
   wherein said first angled adaptor is removably secured to the either the first inlet or the second inlet through aligning each outer protrusion of the first angled adaptor with one cutout of the plurality of cutouts of either the first inlet or the second inlet and pushing the first angled adaptor inward until each protrusion of the first angled adaptor reaches the intermediate point of the first inlet or the second inlet and then twisting the first angled adaptor either to the left or right depending on the location of the aperture of the first inlet or the second inlet with respect to an associated cutout which causes each protrusion of the first angled adaptor to mate with the apertures of the first inlet or the second inlet such that the first angled adaptor cannot be pulled out unless the first angled adaptor is twisted in the opposite direction;

wherein said second valve adaptor is removably secured to the either the first inlet or the second inlet through aligning each outer protrusion of the second valve adaptor with one cutout of the plurality of cutouts of either the first inlet or the second inlet and pushing the second valve adaptor inward until each protrusion of the second valve adaptor reaches the intermediate point of the first inlet or the second inlet and then twisting the second valve adaptor either to the left or right depending on the location of the aperture of the first inlet or the second inlet with respect to an associated cutout which causes each protrusion of the second valve adaptor to mate with an associated aperture of the first inlet or the second inlet such that the second valve adaptor cannot be pulled out unless the second valve adaptor is twisted in the opposite direction.

8. The delivery device of claim 1 wherein said second valve adaptor including a housing having an inlet end having an outer extending flange serving as a safety ring, said outer extending flange having an outer diameter large enough to prevent or make it difficult to inadvertently secure a corrugated oxygen tubing associated with a source of medical gas to the inlet end of the second valve adaptor.

9. The delivery device of claim 1 wherein said second valve adaptor including a housing having a valve member comprising a valve cover and valve stem, said housing constructed from a translucent, clear or transparent material and said valve cover and valve stem constructed from a dark colored material to permit a user to determine whether the valve cover and valve stem are properly moving during use.

10. A method for using the multiple pieces delivery device of claim 1 by a user regardless of a physical position or medical condition of the user, the method comprising:
(a) providing the manifold member having the first inlet, the second inlet, the intermediate member and the single outlet;
(b) removably securing the first angled adaptor in one of two possible orientations to the first inlet or removably securing the first angled adaptor in one of two possible orientations to the second inlet based on a current physical position or medical condition of the user; and
(c) removably securing the second valve adaptor to either the first inlet or the second inlet depending on which inlet of the manifold member the first angled adaptor is to be removably secured to.

11. A multiple pieces delivery device for mixing a plurality of separately received content and delivering the mixed content to a single outlet, comprising:
a manifold member having a first inlet, a second inlet, an intermediate member and the single outlet, wherein the first inlet in internal communication with the intermediate member and the second inlet separately in internal communication with the intermediate member, wherein the first inlet and the second inlet are isolated from each other before being in communication at the intermediate member, said outlet in internal communication with the intermediate member, the first inlet being linear or straight from a first end to a second end of the first inlet and the second inlet being linear or straight from a first end to a second end of the second inlet;
a first angled adaptor removably secured to either the first inlet or the second inlet of the manifold member, the first angled adaptor having a pair of outer securement protrusions, the first angle adaptor can be removably secured to the first inlet in a plurality of different orientations with respect to the manifold member and can be removably secured to the second inlet in a plurality of different orientations with respect to the manifold member; and
a second valve adaptor removably secured to either the second inlet or the first inlet of the manifold member, the second valve adaptor having a pair of outer securement protrusions;
wherein a first content is configured to travel through said first angled adaptor and ultimately received within the intermediate member and a second content is configured to travel through said second valve adaptor and ultimately received within the intermediate member and mixed with the first content wherein a mixture of the first content and the second content is configured to enter the outlet from the intermediate member;
wherein the first inlet having an opening at an outer edge and a side wall defining an adaptor receiving area beginning at the outer edge of the first inlet and extending within the first inlet, the side wall of the first inlet having a pair of apertures that are separate from the opening at the outer edge of the first inlet and allow the first angled adaptor or the second valve adaptor to be removably secured to the first inlet and allow the first angled adaptor to be removably secured at the first inlet in a plurality of orientations with respect to the manifold member; and
wherein the second inlet having an opening at an outer edge and a side wall defining an adaptor receiving area beginning at the outer edge of the second inlet and extending within the second inlet, the side wall of the second inlet having a pair of apertures that are separate from the opening at the outer edge of the second inlet and allow the first angled adaptor or the second valve adaptor to be removably secured to the second inlet and allow the first angled adaptor to be removably secured at the second inlet in a plurality of orientations with respect to the manifold member;
wherein multiple securement orientations and locations of the first angled adaptor and the second valve adaptor to the manifold member allow for at least four separate content delivery positions for the first angled adaptor and second valve adaptor with respect to the manifold member to accommodate varying physical positions or a medical condition of a user of the multiple piece delivery device;
wherein the first angled adaptor is removably secured to the first inlet in one of two possible orientations through the mating of the pair of outer protrusions of the first angled adaptor with the pair of apertures of the first inlet or said first angled adaptor is removably secured to the second inlet in one of two possible orientations through the mating of the pair of outer protrusions of the first angled adaptor with the pair of apertures of the second inlet;
wherein the second valve adaptor is removably secured to the first inlet through the mating of the pair of outer protrusions of the second valve adaptor with the pair of apertures of the first inlet or the second valve adaptor is removably secured to the second inlet through the mating of the pair of outer protrusions of the second valve adaptor with the pair of apertures of the second inlet.

12. The multiple pieces delivery device of claim 11 wherein the manifold member is a y-shaped manifold member with the first inlet disposed at a non-perpendicular angle with respect to the second inlet and the second inlet and outlet collinear with each other.

13. The multiple pieces delivery device of claim 11 wherein the second valve adaptor including a housing having an inlet end having an outer extending flange serving as a safety ring, said outer extending flange having an outer diameter large enough to prevent or make it difficult to inadvertently secure a corrugated oxygen tubing associated with a source of medical gas to the inlet end of the second valve adaptor.

14. The multiple pieces delivery device of claim 11 wherein the second valve adaptor including a housing having a valve member comprising a valve cover and valve stem, the housing constructed from a translucent, clear or transparent material and said valve cover and valve stem constructed from a dark colored material to permit a user to determine whether the valve cover and valve stem are properly moving during use.

15. The multiple pieces delivery device of claim 11 wherein the side wall of the first inlet having a pair of internal cutouts with each cutout extending from the outer edge of the first inlet up to an intermediate point of the first inlet; wherein each of the pair of internal cutouts of the first inlet located adjacent to a side of one aperture of the pair of apertures of the first inlet;
   wherein the side wall of the second inlet having a pair of internal cutouts with each cutout extending from the outer edge of the second inlet up to an intermediate point of the second inlet;
   wherein each of the pair of internal cutouts of the second inlet located adjacent to a side of one aperture of the pair of apertures of the second inlet.

16. The multiple pieces delivery device of claim 15 wherein the first angled adaptor is removably secured to the either the first inlet or the second inlet through aligning each outer protrusion of the first angled adaptor with one cutout of the pair of cutouts of either the first inlet or the second inlet and pushing the first angled adaptor inward until each protrusion of the first angled adaptor reaches the intermediate point of the first inlet or the second inlet and then twisting the first angled adaptor either to the left or right depending on the location of the aperture of the first inlet or the second inlet with respect to an associated cutout which causes each protrusion of the first angled adaptor to mate with the apertures of the first inlet or the second inlet such that the first angled adaptor cannot be pulled out unless the first angled adaptor is twisted in the opposite direction;
   wherein the second valve adaptor is removably secured to the either the first inlet or the second inlet through aligning each outer protrusion of the second valve adaptor with one cutout of the pair of cutouts of either the first inlet or the second inlet and pushing the second valve adaptor inward until each protrusion of the second valve adaptor reaches the intermediate point of the first inlet or the second inlet and then twisting the second valve adaptor either to the left or right depending on the location of the aperture of the first inlet or the second inlet with respect to an associated cutout which causes each protrusion of the second valve adaptor to mate with an associated aperture of the first inlet or the second inlet such that the second valve adaptor cannot be pulled out unless the second valve adaptor is twisted in the opposite direction.

17. The multiple pieces delivery device of claim 1 wherein the first inlet being linear or straight from a first end to a second end of the first inlet and the second inlet being linear or straight from a first end to a second end of the second inlet.

\* \* \* \* \*